US010206921B2

(12) United States Patent
Carmichael et al.

(10) Patent No.: US 10,206,921 B2
(45) Date of Patent: Feb. 19, 2019

(54) METHODS AND COMPOSITIONS FOR TREATING A SUBJECT FOR CENTRAL NERVOUS SYSTEM (CNS) INJURY

(75) Inventors: Stanley T. Carmichael, Sherman Oaks, CA (US); Istvan Mody, Los Angeles, CA (US); Andrew Clarkson, Los Angeles, CA (US); Ben Huang, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 734 days.

(21) Appl. No.: 12/793,607

(22) Filed: Jun. 3, 2010

(65) Prior Publication Data

US 2011/0224278 A1    Sep. 15, 2011

Related U.S. Application Data

(60) Provisional application No. 61/183,898, filed on Jun. 3, 2009.

(51) Int. Cl.
*A61K 31/00* (2006.01)
*A61K 31/5025* (2006.01)
*A61K 31/551* (2006.01)
*A61K 31/5517* (2006.01)
*A61K 31/713* (2006.01)

(52) U.S. Cl.
CPC ........ *A61K 31/5025* (2013.01); *A61K 31/551* (2013.01); *A61K 31/5517* (2013.01); *A61K 31/713* (2013.01)

(58) Field of Classification Search
USPC .................................. 514/44, 220, 245, 219
See application file for complete search history.

(56) References Cited

U.S. PATENT DOCUMENTS

| 2004/0082555 | A1 | 4/2004 | Villalobos |
| 2006/0018839 | A1 | 1/2006 | Ieni et al. |
| 2007/0112017 | A1* | 5/2007 | Barlow et al. ................ 514/282 |

FOREIGN PATENT DOCUMENTS

| CA | 2015336 A1 | 11/1990 |
| WO | WO-03/006471 A1 | 1/2003 |
| WO | WO-2006/063708 A1 | 6/2006 |
| WO | WO-2007/018660 A2 | 2/2007 |
| WO | WO-2007/053596 A1 | 5/2007 |
| WO | WO-2009/100040 A2 | 8/2009 |

OTHER PUBLICATIONS

Atack et al, Neuropharmacology, 51 (2006), 1023-1029.*
Tatemichi et al, Journal of Neurology, Neurosurgery and Psychiatric 1994,;57:202-207.*
Shimamura et al, Stroke, 2007;38:3251-3258.*
International Search Report and Written Opinion for PCT/US11/38965, dated Nov. 30, 2011.
Krehan et al. "Potent 4-Arylalkyl-Substituted 3-Isothiazolol GABAA Competitivel Noncompetitive Antagonists: Synthesis and Pharmacology." J Med Chem., 2006, vol. 49(4), pp. 1388-1396; Abstract only, http://pubs.acs.org/doi/abs/10.1021/jm0509871.
Pavlov et al. "Outwardly Rectifying Tonically Active GABAA Receptors in Pyramidal Cells Modulate Neuronal Offset, Not Gain." The Journal of Neuroscience, 2009, vol. 29(48), pp. 15341-15350; p. 15341 http://www.jneurosci,org/contenti29/48/15341.fulLpdf+html.
Savic et al. "PWZ-029, a compound with moderate inverse agonist functional selectivity at GABAA receptors containing alpha 5 subunits, improves passive, but not active, avoidance learning in rats." Brain Research, 2008, vol. 1208, pp. 150-159; Abstract only, http://www.sciencedirect.com/science/article/pii/S000689930800365X.
Braun et al. "Spatiotempeoral relationship of apoptotic cell death to lymphomonocytic infiltration in photocehmically induced focal ischemia of the rat cerebral cortex" Acta Neuropathol (1996) 92: 255-263.
Carmichael S. "Plasticity of Cortical Projections after Stroke" Department of Neurology, David Geffen School of Medicine, UCLA; The Neuroscientist (2003) vol. 9, No. 1; pp. 64-75.
Carmichael, S. "Cellular and Molecular Mechanisms of Neural Repair after Stroke: Making Waves" Annals of Neurology (2006) vol. 59, No. 5; pp. 735-742.
Chambers et al., "6.7-Dihydro-2-benzothiophen-4(5H)-ones: A Novel Class of GABA-A a5 Receptor Inverse Agonists" J. Med Chem (2002) 45, 1176-1179.
Frahm et al., "Stable expression of the vesicular gaba transporter following photothrombotic infarct in rat brain" Neuroscience 140 (2006) 865-877.
Quirk et al., "[3H] L-655,708, a Novel Ligand Selective for the Benzodiazepine Site of GABA Receptors which Contain the x5 Subunit" Neuropharmacology vol. 35, No. 9/10 (1996) pp. 1331-1335.
Zhou et al., "Neuroprotection of y-Aminobutyric Acid Receptor Agonists Via Enhancing Neuronal Nitric Oxide Synthase (Ser847) Phosphorylation Through Increased Neuronal Nitric Oxide Synthase and PSD95 Interaction and Inhibited Protein Phosphatase Activity in Cerebral Ischemia", Journal of Neuroscience Research, 86:2973-2983 (2008).
Clarkson et al., "639.I/Q8: Suppressing tonic inhibition in vivo mediates post-stroke functional improvements." Abstracts of the Annual Meeting of the Society for Neuroscience; 39th Annual Meeting of the Society-For-Neuroscience, Society for Neuroscience, Washington, DC, US; Chicago, IL, USA, vol. 39, Jan. 1, 2009 (Jan. 1, 2009), p. 639.

(Continued)

*Primary Examiner* — Jean P Cornet
(74) *Attorney, Agent, or Firm* — Foley & Lardner LLP

(57) ABSTRACT

Methods for treating a central nervous system (CNS) injury in a subject are provided. Aspects of the methods include administering to the subject an effective amount of gamma aminobutyric acid (GABA) receptor signaling inhibitor to treat the subject for the CNS injury. Also provided are compositions finding use in embodiments of the methods. Methods and compositions of the invention find use in the treatment of a variety of different CNS injuries, including but not limited to, treating a subject for CNS injury associated with the occurrence of stroke.

15 Claims, 10 Drawing Sheets

(56) References Cited

OTHER PUBLICATIONS

Huang et al., "639.3/Q10: Post-stroke elevation of tonic inhibition is associated with specific down-regulation of GABA transporters in peri-infarct cortex." Abstracts of the Annual Meeting of the Society for Neuroscience; 39th Annual Meeting of the Society-For-Neuroscience, Society for Neuroscience, Washington, DC, US; Chicago, IL, USA, vol. 39, Jan. 1, 2009 (Jan. 1, 2009).
Andrew N. Clarkson et al., "Reducing excessive GABA—mediated tonic inhibition promotes functional recovery after stroke," Nature, vol. 468: 305-311 (2010).
European Search Report for European Application No. 11790427.6 dated Dec. 11, 2013.
Lipton, P. "Ischemic Cell Death in Brain Neurons." Physiological Reviews, 79(4):1431-1568 (1999).

\* cited by examiner

METHODS AND COMPOSITIONS FOR TREATING A SUBJECT FOR CENTRAL NERVOUS SYSTEM (CNS) INJURY

CROSS-REFERENCE TO RELATED APPLICATIONS

Pursuant to 35 U.S.C. § 119(e), this application claims priority to U.S. Provisional Application Ser. No. 61/183,898, filed Jun. 3, 2009; the disclosure of which is herein incorporated by reference.

STATEMENT OF GOVERNMENT SUPPORT

This invention was made with Government support under Grant No. NS030549, awarded by the National Institutes of Health. The Government has certain rights in this invention.

INTRODUCTION

Injuries to the brain or spinal cord from stroke, trauma or neurodegenerative disease produce loss of behavioral function and limited recovery. Damage to the brain or spinal cord produces loss of function in two ways. First, the injury causes complete damage at the center of the insult to neural circuits that control a bodily function, like movement, sensation or language. Second, the injury causes partial damage to neural circuits that are adjacent to the injury site (termed peri-infarct tissue), and disables the function of these circuits. Most therapies in CNS injury and stroke have been directed toward the first mechanism of damage: preventing the initial injury or cell death (an approach termed neuroprotection). No therapies have been directed at stabilizing partially damaged circuits in the brain, and promoting their function.

Stroke and other forms of CNS injury not only cause complete damage at the center of the insult, they also cause partial damage to adjacent areas. Neurons in these areas lose some of their connections. Their processes, or dendrites, can become stunted, malformed or exhibit altered turnover of their cellular contacts (Brown C E, Li P, Boyd J D, Delaney K R, Murphy T H (2007) Extensive turnover of dendritic spines and vascular remodeling in cortical tissues recovering from stroke. J. Neurosci. 27:4101-9; Brown C E, Wong C, Murphy T H (2008) Rapid morphologic plasticity of peri-infarct dendritic spines after focal ischemic stroke. Stroke. 39:1286-91). The abnormal structure and activity of neurons adjacent to the stroke site means that the ability of these cells to perform normal cognitive operations in the brain, such as forming motor, sensory or language maps, is reduced. The tissue that surrounds the stroke site is neurologically "disabled".

The ability of these partially damaged cells to send signals in the brain is also altered by this partial damage. These cells fire abnormal signals to incoming information and exhibited altered responses to excitatory input (Carmichael S T (2003) Cortical plasticity after stroke. Neuroscientist. 9:64-75.). The ability of these neurons to regulate neurotransmitters is altered, with reduced levels of proteins that take up GABA from the extracellular space (Frahm C, Siegel G, Grass S, Witte O W (2006) Stable expression of the vesicular GABA transporter following photothrombotic infarct in rat brain. Neuroscience. 140:865-77). As a result GABA may accumulate or have an enhanced function after stroke.

The current state of the art in pharmacological stroke treatment is limited to acute intravenous administration of the thrombolytic drug, tissue plasminogen activator (tPA). tPA works by dissolving blood clots and opening brain blood vessels. tPA is thus a "neuroprotective" therapy because it works by restoring blood flow and preventing ischemic cell death in the brain. tPA confers a modest behavioral benefit in functional recovery, but has a very narrow therapeutic window. tPA must be delivered within 4.5 hours from the time the patient suffers a stroke, otherwise the risks associated with tPA administration outweigh any potential benefit. At present this time window precludes administration of tPA to approximately 90% of all stroke patients (Dávalos A (2005) Thrombolysis in acute ischemic stroke: successes, failures, and new hopes. Cerebrovasc Dis. 20 Suppl 2:135-9).

Furthermore, this treatment is only effective in a subset of stroke patients. For example, tPA is not an appropriate treatment option following hemorrhagic stroke, as the "clot busting" features of the drug can exacerbate the bleeding in this type of stroke. Finally, tPA is not a recovery or rehabilitative treatment, but rather a neuroprotection treatment (Bambauer K Z, Johnston S C, Bambauer D E, Zivin J A (2006) Reasons why few patients with acute stroke receive tissue plasminogen activator. Arch Neurol. 63:661-4; Weintraub M I (2006) Thrombolysis (tissue plasminogen activator) in stroke: a medicolegal quagmire. Stroke. 37:1917-22). There is no currently approved pharmacological or other medical treatment that promotes recovery after CNS injury. The primary rehabilitative treatment after CNS injury is physical rehabilitation: physical, occupational and speech therapy. This therapy is expensive, labor-intensive, time consuming and not available equally to all patients (Dobkin, B. 2003 The Clinical Science of Neurological Rehabilitation. Oxford Univ. Press:Oxford).

SUMMARY

Methods for treating a central nervous system (CNS) injury in a subject are provided. Aspects of the methods include administering to the subject an effective amount of gamma aminobutyric acid (GABA) receptor signaling inhibitor to treat the subject for the CNS injury. Also provided are compositions finding use in embodiments of the methods. Methods and compositions of the invention find use in the treatment of a variety of different CNS injuries, including but not limited to, treating a subject for CNS injury associated with the occurrence of stroke.

BRIEF DESCRIPTION OF THE DRAWINGS

FIG. 1A. Images showing the peri-infarct recording site. FIG. 1B. Box-plot (boxes: 25-75%, whiskers: 10-90%, lines: median) showing significantly elevated tonic inhibition in peri-infarct cortex (asterisk: P<0.05). FIGS. 1C and 1D. Representative traces showing the tonic inhibitory currents in control and peri-infarct neurons, respectively.

FIG. 2A. Blocking GAT-1 by NO-711 (10 μM) increased Itonic in post-stroke neurons more than in controls. Co-application of NO-711 and SNAP-5114, produced a substantial Itonic increase in controls. FIGS. 2B and 2C. Representative recordings showing sequential drug applications in control and peri-infarct neurons, respectively. FIG. 2D. Representative recording showing the effect of L655,708 (100 nM) in reducing Itonic. FIG. 2E. provides graphical results of data obtained as described below. FIG. 2F. L655, 708 significantly decreased post-stroke Itonic, and notably reverted Itonic to near-control level.

FIG. 4A. Western blot of GAT-1 (top) and GAPDH (protein loading control, bottom). FIG. 4B. Western blot of GAT-3/4 (top) and GAPDH (bottom). FIG. 4C. Quantification of GAT-1 protein level in a ratio to GAPDH in control and stroke. FIG. 4D. Quantification of GAT-3/4 protein level in a ratio to GAPDH (1/GAPDH) in control and stroke.

FIG. 6A. Forelimb function in the grid-walking task: FIG. 6B. Hindlimb function in the grid-walking task. FIG. 6C. Forelimb function in the "cylinder task".

FIG. 7A. Schematic of dorsal view of mouse brain. FIG. 7B. Stroke+vehicle (blue); stroke+L655,708 (red). FIG. 7C. Stroke+EphA5-Fc (Red) and Stroke+vehicle (blue).

FIG. 8A. Grid-walking function for forelimb. FIG. 8B. Grid-walking function for hindlimb. FIG. 8C. Cylinder task function FIG. 9A. Grid-walking function for forelimb. FIG. 9B. Grid-walking function for hindlimb. FIG. 9C. Cylinder task function.

FIG. 10A. Grid-walking function for forelimb. FIG. 10B. Grid-walking function for hindlimb. FIG. 10C. Cylinder task function.

DEFINITIONS

Figure 1:
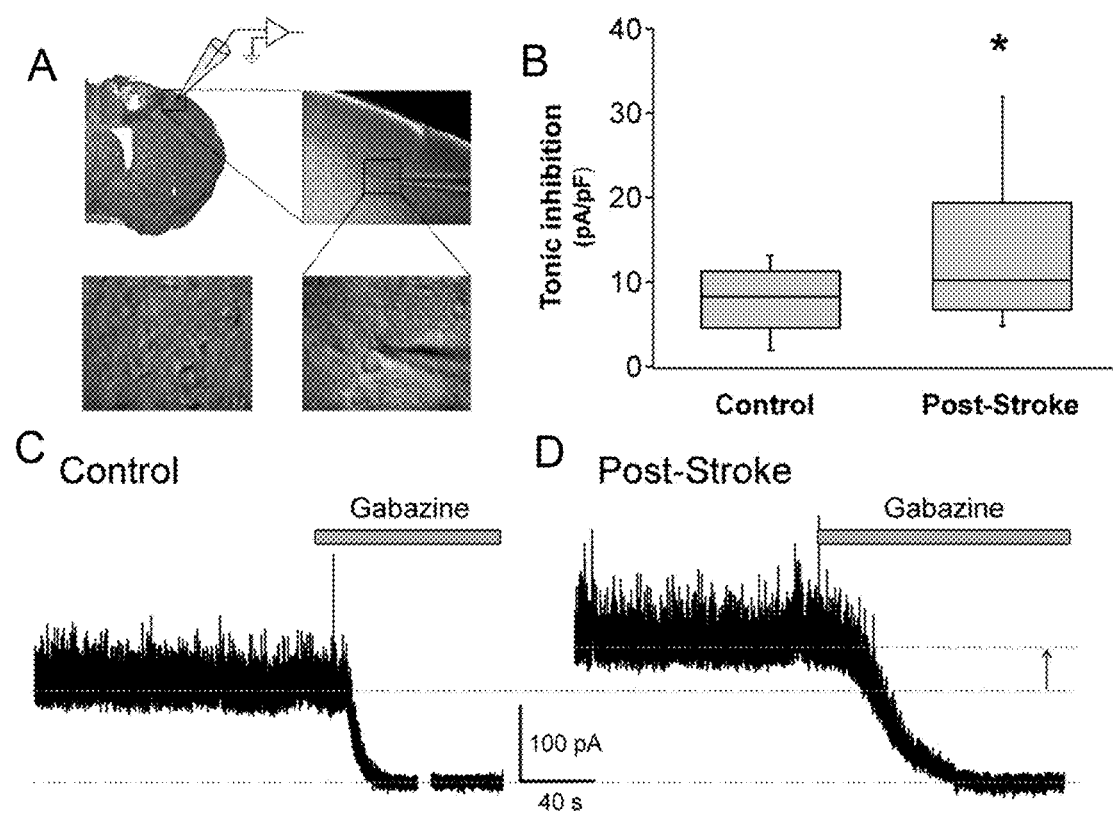
FIGS. 1A-1D illustrate elevated tonic inhibition in peri-infarct cortex.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual", "subject", "host", and "patient", are used interchangeably herein and refer to any mammalian subject for whom diagnosis, treatment, or therapy is desired. In some embodiments, the subjects are humans.

"In combination with" as used herein refers to uses where, for example, the first compound is administered during the entire course of administration of the second compound; where the first compound is administered for a period of time that is overlapping with the administration of the second compound, e.g., where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

A "pharmaceutically acceptable carrier" means carrier that is useful in preparing a pharmaceutical composition that is generally safe, non-toxic and neither biologically nor otherwise undesirable, and include carriers that are acceptable for veterinary use as well as human pharmaceutical use. A pharmaceutically acceptable carrier as used in the specification and claims includes both one and more than one such carrier.

As used herein, a "pharmaceutical composition" is meant to encompass a composition suitable for administration to a subject, such as a mammal, especially a human. A "pharmaceutical composition" may be sterile and free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

DETAILED DESCRIPTION

Methods for treating a central nervous system (CNS) injury in a subject are provided. Aspects of the methods include administering to the subject an effective amount of gamma aminobutyric acid (GABA) receptor signaling inhibitor to treat the subject for the CNS injury. Also provided are compositions finding use in embodiments of the methods. Methods and compositions of the invention find use in the treatment of a variety of different CNS injuries, including but not limited to, treating a subject for CNS injury associated with the occurrence of stroke.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or'testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention, embodiments of methods of the invention are reviewed first, followed by a review of illustrative applications in which the methods may find use, as well as a review of embodiments of various compositions, e.g., pharmaceutical compositions and kits, the find use in practicing embodiments of methods of the invention.

Methods for Treating CNS Injury

As summarized above, aspects of the invention include methods of treating a central nervous system (CNS) injury in a subject. The target CNS injury is, in some embodiments, one that is characterized by the presence of physically damaged or altered CNS tissue. As such, in some instances the target CNS injury is one in which physically damaged tissue, e.g., physically compromised tissue, is present. In some instances the target CNS injury is one in which altered CNS tissue, e.g., CNS tissue is changed in some manner compared to a control (i.e., corresponding CNS tissue from a healthy subject, such as a healthy human) is present. In some embodiments, the CNS injury is characterized by increased GABA receptor signaling in peri-infarct tissue. By increased GABA receptor signaling is meant signaling that is 2-fold or greater, such as 5-fold or greater, than signaling observed in a suitable control.

In some instances, the target CNS injury is one that has been caused by a pathological condition, e.g., a condition caused by disease. The CNS injury may be one that is caused by a variety of different types of pathological conditions, including combinations of two or more pathological conditions. Pathological conditions which may cause target CNS injuries that are treated in accordance with the embodiments of the present invention include, but are not limited to:

trauma, multiple sclerosis, cerebral vasospasm, status epilepticus, perinatal asphyxia, anoxia, Alzheimer's disease, Parkinson's disease, Huntington's disease, cerebral ischemia, cerebral infarction, ischemic brain damage, spinal cord injury, tissue ischemia, reperfusion injury or any other CNS injury resulting in physical damage to CNS tissue and combinations thereof.

In certain embodiments, the CNS injury is one that has been caused by a stroke. By "stroke" is meant, any condition that results in physical damage to the central nervous system due to disturbance in the blood supply or oxygen to the brain. This can be due to ischemia (lack of blood supply or oxygen) caused by thrombosis or embolism or due to a hemorrhage.

As summarized above, aspects of the invention include administering to the subject an effective amount of a gamma aminobutyric acid (GABA) receptor signaling inhibitor to treat the subject for the CNS injury. Gamma aminobutyric acid (GABA) receptor signaling inhibitors of interest are compounds that, upon administration to the subject, at least reduce gamma aminobutyric acid (GABA) receptor signaling. As compared to a suitable control, e.g., a placebo, administration of GABA receptor signaling inhibitor compound in accordance with methods of the invention results in at least a 2-fold reduction in signaling, such as a 5-fold or greater, 10-fold or greater, including 25-fold or greater reduction in signaling. In some instances, GABA receptor signaling is completely stopped upon administration of the GABA receptor signaling inhibitor.

The GABA receptor signaling that is inhibited by the inhibitor may vary. The neurotransmitter GABA signals in two different ways to produce inhibition to neurons in the CNS. GABA is released from neurons through synaptic receptors when these neurons send signals to other neurons. The released GABA causes a brief inhibitory signal to be passed from the sending neuron to the receiving neuron. This inhibitory signal is synaptic: GABA is released from the sending neuron at the synapse between sending and receiving neurons in the brain. GABA receptors of particular subunit composition also respond to the normal amounts of GABA that are present in the extracellular space, and this GABA activity mediates a tonic or always-on form of inhibition on neurons. This activity causes a chronic low level of a shunting current, which reduces the likelihood that the neuron will fire signals in response to any given input. The GABA receptors mediating this type of conductance show reduced desensitization, so that they will remain active for long periods.

The nature of the GABA receptor that is targeted by the signaling inhibitor may vary. In some instances, the GABA receptor that is targeted by the signaling inhibitor is a basal or tonic GABA receptor. The targeted GABA receptor may be a basal or tonic GABA receptor in the hippocampus and cortex. Accordingly, the targeted GABA receptor may contain α5 or/and δ subunits (in combinations such as, but not limited to, α5βγ2, α4βδ and α6βδ) (e.g., as reported in Glykys J, Mody I (2007) Activation of GABAA receptors: views from outside the synaptic cleft. Neuron. 56:763-70; and Olsen R W, SIEGHART W (2008) International Union of Pharmacology. LXX. Subtypes of γ-Aminobutyric Acid A Receptors: Classification on the Basis of Subunit Composition, Pharmacology, and Function. Update Pharmacol Rev 60:243-260). Aspects of the invention therefore include treating CNS injury by decreasing the activity of tonically active GABA receptors, e.g., GABA receptors with α5 or δ subunits, by administering an inhibitor of GABA receptors with α5 or δ subunits.

The nature of the GABA receptor signaling inhibitor may vary. In some instances, the agent is an agent that modulates, e.g., inhibits, GABA receptor signaling activity by binding to the target GABA receptor. For example, small molecules that bind to the target GABA receptor and inhibit its signaling are of interest. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

The inhibitor of GABA receptor signaling inhibitor may be an inhibitory ligand of a GABA receptor. In certain embodiments, the inhibitor of GABA receptor signaling inhibits the basal or tonic GABA signaling. Embodiments of GABA receptor inhibitory ligands of the invention include small molecule inverse agonists or antagonists. By "inverse agonist" is meant any agent which binds to the same receptor binding-site as an agonist for that receptor and reverses activity of the receptor. As such, inverse agonists exert the opposite pharmacological effect of a receptor agonist. In some instances, the GABA receptor inverse agonist may be L655,708, α5IA, PWZ-029, 6,6-Dimethyl-3-(2-hydroxyethyl)thio-1-(thiazol-2-yl)-6,7-dihydro-2-benzothiophen-4 (5H)-one, RO4938581, mixtures thereof and pharmaceutically acceptable salts thereof.

In other embodiments, the GABA receptor inhibitory ligand of the invention may be a small molecule antagonist. By receptor "antagonist" is meant any type of receptor ligand and/or drug that does not alone provoke a biological response upon binding to a receptor, but blocks or dampens agonist-mediated responses. Antagonists may have affinity but no efficacy for their cognate receptors, and binding may disrupt the interaction and inhibit the function of an agonist or inverse agonist at the receptors. In exemplary embodiments, the receptor antagonist of the invention may be Xli093.

Inhibitory ligands of GABA signaling of interest include, but are not limited to, those provided in Table 1 below.

TABLE 1

| GABA$_A$ Receptor Activity | Trade Name | Chemical Name | Synthesis | Structure |
|---|---|---|---|---|
| α5 inverse agonists | L655,708 | | Quirk et al. Neurpharmacology 35: 1331 (2002); Chambers et al; J Med Chem. 45: 1176 (2002) | 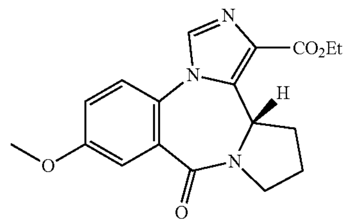 [SMILES: CCOC(=O)c1ncn2c1[C@@H]1CCCN1C(=O)c1cc(OC)ccc1-2] |
| | PWZ-029 | methyl(8-chloro-5,6-dihydro-5-methyl-6-oxo-4Himidazo[1,5-α][1,4]benzodiazepin-3-yl)methyl ether), SH-053-R-CH3-2'F (the (R) stereoisomer of 8-ethynyl-6-(2-fluorophenyl)-4-methyl-4H-2,5,10b-triaza-benzo[e]azulene-3-carboxylic acid ethyl ester) | Savić et al Brain Research 1208: 150 (2008) | |
| | A5iaII | 3-(5-methylisoxazol-3-yl)-6-(2-pyridyl)methyloxy-1,2,4-triazolo[3,4-a]phthalazine | Street et al J Med Chem 47: 3642 (2004) | |
| | A5iaI | 3-(5-methylisoxazol-3-yl)-6-[(1-methyl-1,2,3-triazol-4-yl)methyloxy]-1,2,4-triazolo[3,4-a]phthalazine | Sternfield et al J Med Chem 47: 2176 (2004) | |

TABLE 1-continued

| GABA$_A$ Receptor Activity | Trade Name | Chemical Name | Synthesis | Structure |
|---|---|---|---|---|
| | MRK-016 | 3-tert-Butyl-7-(5-methylisoxazol-3-yl)-2-(1-methyl-1H-1,2,4-triazol-5-ylmethoxy)-pyrazolo[1,5-d]-[1,2,4]triazine | Atack et al. J Pharm Exp Therap. 331: 470 (2009); Chambers et al J Med Chem 47: 5829 (2004) | |
| | Ro15-4513 | 8-Azido-5,6-dihydro-5-methyl-6-oxo-4H-imidazo[1,5-a][1,4]benzodiazepine-3-carboxylic acid ethyl ester | Suzdak et al. Science 234 1243 (1986) | |
| | RY-080 | ethyl 8-ethynyl-5,6-dihydro-5-methyl-6-oxo-4H-imidazo[1,5-a][1,4]benzodiazepine-3-carboxylate | Liu et al. J. Med. Chem. 39: 1928 (1996) | |
| | RY-023 | t-butyl 8[(trimethylsilyl)ethynyl]-5,6-dihydro-5-methyl-6-oxo-4H-imidazo[1,5-a][1,4]benzodiazepine-3-carboxylate | Liu et al. J. Med. Chem. 39: 1928 (1996) | |
| | RY-024 | t-butyl 8-ethynyl-5,6-dihydro-5-methyl-6-oxo-4H-imidazo[1,5-a][1,4]benzodiazepine-3-carboxylate | Huang et al J Med Chem 41: 4130 (1998) | |
| | RY-010 | ethyl 8-ethyl-5,6-dihydro-5-methyl-6-oxo-4H-imidazo[1,5-a][1,4]benzodiazepine-3-carboxylate | Liu et al. J. Med. Chem. 39: 1928 (1996) | |

TABLE 1-continued

| GABA$_A$ Receptor Activity | Trade Name | Chemical Name | Synthesis | Structure |
|---|---|---|---|---|
| | RO19-4603 | 5,6-Dihydro-5-methyl-6-oxo-4H-imidazo[1,5-a]thieno[2,3-f][1,4]diazepine-3-carboxylic acid 1,1-dimethylethyl ester | Balakleevsky et al Alcohol <& Alcoholism. 25: 449 (1990) | |
| | RO4938581 | | Knust et al Bioorganic & Medicinal Chemistry Letters 19: 5940 (2009) | |
| | RO4882224 | | Knust et al Bioorganic & Medicinal Chemistry Letters 19: 5940 (2009) | |
| GABA antagonists | | | | |
| | RO15-1788 | | | |

GABA receptor signaling inhibitors also include agents that reduce the expression of a target GABA receptor(s). By reducing expression is meant that the inhibitor decreases the amount of active GABA receptor, e.g., by 2-fold or more, such as 5-fold or more, including 10-fold or more, as compared to a suitable control. GABA receptor expression reducing inhibitors of interest include, but are not limited to: small molecules, nucleic acids and peptides or proteins. For example, GABA receptor expression reducing inhibitors agents of interest may include: antisense agents, RNAi agents, agents that interfere with transcription factor binding to a promoter sequence of a gene encoding a subunit of GABA receptor, or inactivation of a gene encoding a subunit of GABA receptor, e.g., through recombinant techniques, etc.

For example, antisense molecules can be used to downregulate expression of the target GABA receptor in the cell. The anti-sense reagent may be antisense oligodeoxynucleotides (ODN), such as synthetic ODN having chemical modifications from native nucleic acids, or nucleic acid constructs that express such anti-sense molecules as RNA. The antisense sequence is complementary to the mRNA of the targeted repressor protein, and inhibits expression of the targeted repressor protein. Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

In addition, the transcription level of a target GABA receptor can be regulated by gene silencing using RNAi agents, e.g., double-strand RNA (Sharp (1999) *Genes and Development* 13: 139-141). RNAi, such as double-stranded RNA interference (dsRNAi) or small interfering RNA (siRNA), has been extensively documented in the nematode *C. elegans* (Fire, A., et al, *Nature,* 391, 806-811, 1998) and routinely used to "knock down" genes in various systems. RNAi agents may be dsRNA or a transcriptional template of the interfering ribonucleic acid which can be used to produce dsRNA in a cell. In these embodiments, the transcriptional template may be a DNA that encodes the interfering ribonucleic acid. Methods and procedures associated with RNAi are also described in WO 03/010180 and WO 01/68836, all of which are incorporated herein by reference. dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety). A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

In another embodiment, the target GABA receptor gene is inactivated so that it no longer expresses a functional protein. By inactivated is meant that the gene, e.g., coding sequence and/or regulatory elements thereof, is genetically modified so that it no longer expresses functional a functional GABA receptor protein, e.g., at least with respect to the targeted GABA receptor signaling. The alteration or mutation may take a number of different forms, e.g., through deletion of one or more nucleotide residues, through exchange of one or more nucleotide residues, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998, 144; 5,948,653; 5,925,544; 5,830,698; 5,780,296; 5,776, 744; 5,721,367; 5,614,396; 5,612,205; the disclosures of which are herein incorporated by reference.

Also of interest in certain embodiments are dominant negative mutants of the target GABA receptor, where expression of such mutants in the cell result in a modulation, e.g., decrease, in the targeted GABA receptor signaling. Dominant negative mutants of GABA receptor are mutant proteins that exhibit dominant negative GABA receptor activity. As used herein, the term "dominant-negative GABA receptor activity" or "dominant negative activity" refers to the inhibition, negation, or diminution of certain particular activities of GABA receptor, and specifically to the targeted GABA receptor signaling. Dominant negative mutations are readily generated for corresponding proteins. These may act by several different mechanisms, including mutations in a substrate-binding domain; mutations in a catalytic domain; mutations in a protein binding domain (e.g. multimer forming, effector, or activating protein binding domains); mutations in cellular localization domain, etc. A mutant polypeptide may interact with wild-type polypeptides (made from the other allele) and form a non-functional multimer. In certain embodiments, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative mutants (see for example, Herskowitz (1987) Nature 329:219, and the references cited above). Such techniques are used to create loss of function mutations, which are useful for determining protein function. Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

In some instances, the expression modulatory inhibitor is a nucleic acid inhibitor. Nucleic acid inhibitors may vary. An inhibitor that may reduce the expression of the GABA receptor may be a small interfering RNA (siRNA) or a short hairpin RNA (shRNA) complementary to all or a portion of a messenger RNA encoding a subunit of the GABA receptor. In certain cases, the inhibitor of GABA receptor signaling may be a siRNA or shRNA complementary to all or a portion of a messenger RNA encoding α subunit of the GABA receptor. In certain cases, the inhibitor of GABA receptor signaling may be a siRNA or shRNA complementary to all or a portion of a messenger RNA encoding δ subunit of the GABA receptor. siRNA or shRNA complementary to all or a portion of a messenger RNA encoding a subunit of the GABA receptor may be administered as compositions containing the siRNA or shRNA in a viral transduction vector, for example.

In practicing methods of the invention, the GABA receptor signaling inhibitor can be administered to the subject using any method and route suitable for delivery of the inhibitor, including systemic or localized routes. Routes of administration may be combined, if desired, or adjusted depending upon the pharmaceutical composition and/or the desired effect.

The inhibitor may be administered using any medically appropriate procedure, e.g., intravascular (intravenous, intraarterial, intracapillary) administration, injection into the cerebrospinal fluid, intracavity or direct injection. Intrathecal administration maybe carried out through the use of an Ommaya reservoir, in accordance with known techniques. (F. Balis et al., Am J. Pediatr. Hematol. Oncol. 11, 74, 76 (1989).

Where local delivery is desired, administration may involve administering the inhibitor to a desired target tissue, such a brain, spine, etc. For local delivery, the administration may be by injection or by placement of a composition containing the inhibitor in the desired tissue or organ by surgery, for example. In certain cases, an implant, such as a cannula implant, that acts to retain the active dose at the site of implantation may be used. In some instances, hydrogel delivery is employed, e.g., as described in Piantino J, Burdick J A, Goldberg D, Langer R, Benowitz L I (2006) An injectable, biodegradable hydrogel for trophic factor delivery enhances axonal rewiring and improves performance after spinal cord injury. Exp Neurol. 201:359-67; and Ma J, Tian W M, Hou S P, Xu Q Y, Spector M, Cui F Z (2007) An experimental test of stroke recovery by implanting a hyaluronic acid hydrogel carrying a Nogo receptor antibody in a rat model. Biomed Mater. 2:233-40. In some instances, systemic, intraperitoneal, intravascular or subcutaneous protocols are employed, e.g., as described in Pardridge W M (2008) Re-engineering biopharmaceuticals for delivery to brain with molecular Trojan horses. Bioconjug Chem. 19:1327-38. In some instances, nanoparticle mediated delivery protocols may be employed, e.g., as described in Tosi G, Costantino L, Ruozi B, Forni F, Vandelli M A (2008) Polymeric nanoparticles for the drug delivery to the central nervous system. Expert Opin Drug Deliv. 5:155-74; and Ulbrich. K, Hekmatara T, Herbert E, Kreuter J (2008) Transferrin- and transferrin-receptor-antibody-modified nanoparticles enable drug delivery across the blood-brain barrier (BBB). Eur J Pharm Biopharm. 2008 Sep. 5. [Epub ahead of print]. In some instances, intracerebral, ventricular or intrathecal delivery protocols may be employed, e.g., as described in Buchli A D and Schwab M E (2005) Inhibition of Nogo: a key strategy to increase regeneration, plasticity and functional recovery of the lesioned central nervous system. Ann Med. 37:556-67; and Shoichet M S, Tator C H, Poon P, Kang C, Baumann M D (2007) Intrathecal drug delivery strategy is safe and efficacious for localized delivery to the spinal cord. Prog Brain Res. 161:385-92. In some instances, intranasal delivery protocols are employed, e.g., as described in Smith P F (2003) Neuroprotection against hypoxia-ischemia by insulin-like growth factor-I (IGF-I). IDrugs. 6:1173-7; and Vyas T K, Tiwari S B, Amiji M M. (2006) Formulation and physiological factors influencing CNS delivery upon intranasal administration. Crit. Rev Ther Drug Carrier Syst. 23:319-47.

In some embodiments, the inhibitor may be formulated to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the inhibitor compositions disclosed herein when the compositions are administered by intravascular injection. Other strategies for transportation across the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to an inhibitor for use in the methods disclosed herein to facilitate transport across the epithelial wall of the blood vessel. Alternatively, drug delivery behind the BBB is by intrathecal delivery of therapeutics directly to the cranium, as through an Ommaya reservoir.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

In some instances, the inhibitor is administered to the subject after the occurrence of the CNS injury, e.g., 1 or more days after the injury occurrence, such as 2 or more days after the injury occurrence. The administering of the inhibitor may be performed 3 days to 30 days after occurrence of the CNS injury. In certain cases, the administering may be performed 3 days to 25 days, or 3 days to 20 days, or 3 days to 15 days, or 3 days to 10 days, or 3 days to 7 days, or after 3 days to 5 days, after the occurrence of the CNS injury. In certain cases, the administering may be performed 5 days to 30 days, or 10 days to 30 days, or 15 days to 30 days, or 20 days to 30 days, or 25 days to 30 days, after the occurrence of CNS injury.

As summarized above, an amount of the inhibitor effective to treat the CNS injury is administered to the subject. Amounts of administered inhibitor may vary depending on a number of factors, such as the particular subject, the particular active agent, the desired treatment and the nature of the CNS injury, etc. An inhibitor of tonically active GABA receptors may be administered based on body size. In some instances, the amount administered may range from 200 µg/kg to 50 mg/kg per day, such as 10 mg/kg to 40 mg/kg per day and including 15 mg/kg to 30 mg/kg per day. This amount may be delivered either locally into the stroke or injury cavity (e.g., with a cannula implant or hydrogel) or systemically, as described above. Compositions containing the inhibitors of the invention as well as dosage forms and amounts are described further below.

In certain cases, after the occurrence of the CNS injury, the subject may be treated with any pharmacological intervention in current practice for tissue protection (e.g., tPA). Following the occurrence of the CNS injury, in the first 3 to 5 days, for example, the patient may be assessed for CNS injury, such as, in the case of a stroke, determining the infarct location and size.

Following delivery of an inhibitor of basal or tonic GABA receptor signaling, the subject may be given standard neuro-rehabilitative therapy and the repair of damaged and/or altered CNS tissue may be assessed. Assessment of reparative or restorative ° effects may include testing for physical (e.g., speech, motor skills, movement of extremities, etc.) and cognitive rehabilitation by any convenient protocol over the course of one, two, four and six weeks after occurrence of CNS injury.

In certain cases, the treatment may further comprise selective targeting of cellular or molecular sites that reduce extracellular GABA levels. These cellular or molecular sites can include GABA uptake systems (GAT1, GAT2, GAT3), GABA synthesizing enzymes (GAD65, GAD67), GABA degrading enzymes (GABA transaminase; GABA-T), vesicular transporters for GABA or release of GABA.

In certain cases, the treatment may further comprise erythropoietin, granulocyte colony stimulating factor (G-CSF), or stem/progenitor cell therapy.

Methods of the invention may be practiced with a variety of different types of subjects. In any of the above methods, the subject may vary. In certain embodiments, the subjects are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits), and primates (e.g., humans, chimpanzees, and monkeys). In certain embodiments, the subjects are humans.

Utility

Embodiments of the methods find use in therapeutic applications in which treatment of CNS injury is indicated. Examples of CNS injuries that may be treated by methods of the invention are disclosed above. In some instances, the target CNS injury is one that has been caused by a pathological condition, e.g., a condition caused by disease. The CNS injury may be one that is caused by a variety of different types of pathological conditions, including combinations of two or more pathological conditions. Pathological conditions which may cause target CNS injuries that are treated in accordance with the embodiments of the present invention include, but are not limited to: trauma, multiple sclerosis, cerebral vasospasm, status epilepticus, perinatal asphyxia, anoxia, Alzheimer's disease, Parkinson's disease, Huntington's disease, cerebral ischemia, cerebral infarction, ischemic brain damage, spinal cord injury, tissue ischemia, reperfusion injury or any other CNS injury resulting in physical damage to CNS tissue and combinations thereof. In certain embodiments, the CNS injury is one that has been caused by a stroke. In some instances, methods and compositions of the invention are employed in the treatment of the causative pathological condition.

By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

The methods may be used in conjunction with other treatment modalities. Embodiments of the invention may be used in conjunction with any current or future therapy for a targeted CNS injury and/or causative pathological condition.

Pharmaceutical Compositions

Provided herein are pharmaceutical compositions of the GABA receptor signaling inhibitor compounds that may be used to inhibit GABA receptor signaling. In pharmaceutical compositions of the invention, inhibitor compounds can be incorporated into a variety of formulations for therapeutic administration by a variety of routes. More particularly, the inhibitor compounds disclosed herein can be formulated into pharmaceutical compositions by combination with appropriate pharmaceutically acceptable carriers. Examples of pharmaceutically acceptable carriers include saline, buffers, diluents, fillers, salts, stabilizers, solubilizers, and other materials which are well known in the art. In some embodiments, the formulations are free of detectable DMSO (dimethyl sulfoxide), which is not a pharmaceutically acceptable carrier.

In certain embodiments, the pharmaceutical composition may be a composition consisting essentially of an inhibitor of GABA receptor signaling and a pharmaceutically acceptable carrier. As used herein, "consisting essentially of" means a pharmaceutical composition that includes inhibitor of GABA receptor signaling and a pharmaceutically acceptable carrier but does not include a nicotine receptor partial agonist or a cholinesterase inhibitor.

In certain embodiments, the inhibitor may be an inhibitory ligand of GABA receptor. In certain embodiments, the inhibitor may be a compound listed in Table 1, or a derivative thereof. The inhibitory ligand may be a GABA receptor inverse agonist or antagonist. The GABA receptor inverse agonist may be a compound selected from the group consisting of L655,708, a5IA, PWZ-029, 6,6-Dimethyl-3-(2-hydroxyethyl)thio-1-(thiazol-2-yl)-6,7-dihydro-2-benzothiophen-4(5H)-one, RO4938581, derivatives thereof, and mixtures thereof. In certain embodiments, two or more inhibitors of GABA receptor signaling may be administered to the subject having CNS injury. The two or more inhibitors may be administered individually or in the same composition.

In pharmaceutical dosage forms, the inhibitor compounds disclosed herein may be administered in the form of their pharmaceutically acceptable salts, or they may also be used alone or in appropriate association, as well as in combination, with other pharmaceutically active compounds.

Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred:

The data obtained from animal studies can be Used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade).

An inhibitor of GABA receptor signaling can be incorporated into a variety of formulations for therapeutic administration. More particularly, the inhibitors disclosed herein can be formulated into pharmaceutical compositions by combination with appropriate pharmaceutically acceptable carriers or diluents, and may be formulated into preparations in solid, semi-solid, liquid or gaseous forms, such as, powders, granules, solutions, injections, inhalants, gels, hydrogels, microspheres, etc.

Hydrogels can be impregnated with the inhibitor for sustained release. Hydrogels may be made with several building blocks, such as, hyaluronan, heparin sulfate, peptides, alginate, agarose, collagen, laminin and glycolic acid, lactic acid, amino acids, etc.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. If oral administration is desired, the subject compounds may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

The subject compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The inhibitor can also be delivered to the subject by enteral administration. Enteral routes of administration include, but are not necessarily limited to, oral and rectal (e.g., using a suppository) delivery. The subject compounds can be made into suppositories by mixing with a variety of bases such as emulsifying bases or water-soluble bases. The suppository can include vehicles such as cocoa butter, carbowaxes and polyethylene glycols, which melt at body temperature, yet are solidified at room temperature.

Depending on the subject and condition being treated and on the administration route, the subject compounds may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery. The composition can be administered in a single dose or in multiple doses.

A typical dosage may be a solution suitable for intravenous administration; a tablet taken from one to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is one which provides up to about 1 µg to about 1,000 µg or about 10,000 µg of subject composition to reduce a symptom in a subject animal.

Unit dosage forms such as syrups; elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

For use in the subject methods, the subject compounds may be formulated with or otherwise administered in combination with other pharmaceutically active agents. Examples of agents that may be used in combination therapy with the compounds described herein include erythropoietin, granulocyte-colony stimulating factor, agents that increase the activity of GABA uptake systems, such as GAT1, GAT2, GAT3; agents that decrease the activity of GABA synthesizing enzymes, such as, GAD65, GAD67; agents that increase the activity of GABA degrading enzymes, such as, GABA transaminase, GABA-T, for example.

The compounds for use in combination therapy with the compounds of the present invention may be administered by the same route of administration. In the alternative, the compounds for use in combination therapy with the compounds of the present invention may be administered by a different route of administration.

The compounds described above may also be administered in combination with other therapies for CNS injury, such as rehabilitative treatment, e.g., physical therapy, occupational therapy, speech therapy, and the like. The compound described above may be administered before, after, or during another rehabilitative treatment for CNS injury.

In certain cases, the inhibitors of the present disclosure are not formulated with or otherwise administered with a nicotine receptor partial agonist or a cholinesterase inhibitor.

Kits

Kits with unit doses of the subject compounds, usually in oral or injectable doses, are provided. In such kits, in addition to the containers containing the unit doses will be an informational package insert describing the use and attendant benefits of the drugs in treating pathological condition of interest. Exemplary compounds and unit doses are those described herein above.

EXPERIMENTAL

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Effect of Stroke on Tonic GABA Signaling

To test the effect of stroke on tonic GABA signaling, patch clamp studies were performed on neurons in motor cortex adjacent to the stroke site (FIGS. 1A to 1D). This region, known as peri-infarct cortex, is the site of the most significant stroke recovery in humans (Carmichael S T (2006) Cellular and molecular mechanisms of neural repair after stroke: making waves. Annal Neurol. 59:735-742).

Whole-cell patch-clamp recordings were made from post-stroke brain slices, within 200 µm of infarct (top left), from layer-2/3 (top right) pyramidal neurons (bottom panels) (FIG. 1A). Cells were voltage-clamped at +10 mV. Box-plot (boxes: 25-75%, whiskers: 10-90%, lines: median) showed significantly elevated tonic inhibition in peri-infarct cortex (asterisk: $P<0.05$) (FIG. 1B). FIGS. 1C and D show representative traces showing the tonic inhibitory currents in control and peri-infarct neurons, respectively. Tonic currents were revealed by the shift in holding currents after blocking all $GABA_A Rs$ with gabazine (>100 µM).

Whole-cell voltage-clamp recordings in in vitro brain slices prepared at 3-, 7- and 14-days post-stroke showed a significant increase in $GABA_A R$-mediated tonic inhibition ($I_{tonic}$) in layer 2/3 pyramidal neurons, compared to neurons from sham controls (control: 8.05±0.80 pA/pF, n=24, vs. post-stroke: 13.6±1.41 pA/pF, n=45, Mann-Whitney U-test, $P<0.05$; FIG. 1B). $I_{tonic}$ remained elevated from 3- to 14-days post-stroke.

Figure 2A:
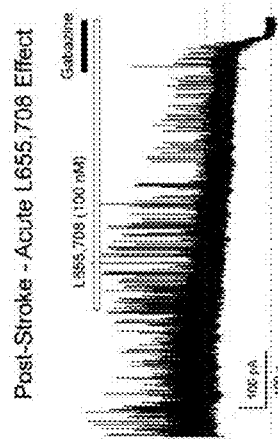
FIGS. 2A-2F depict post-stroke impairment in GABA transport and the effect of blocking α5GABAA receptor.
Figure 2B:
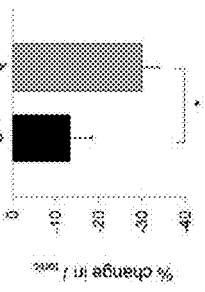
Figure 2C:
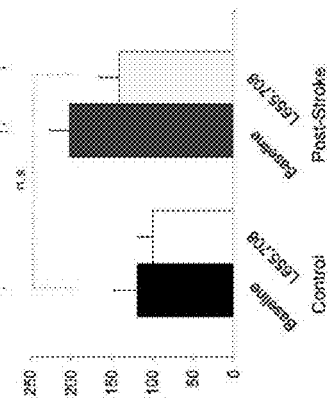
Figure 2D:
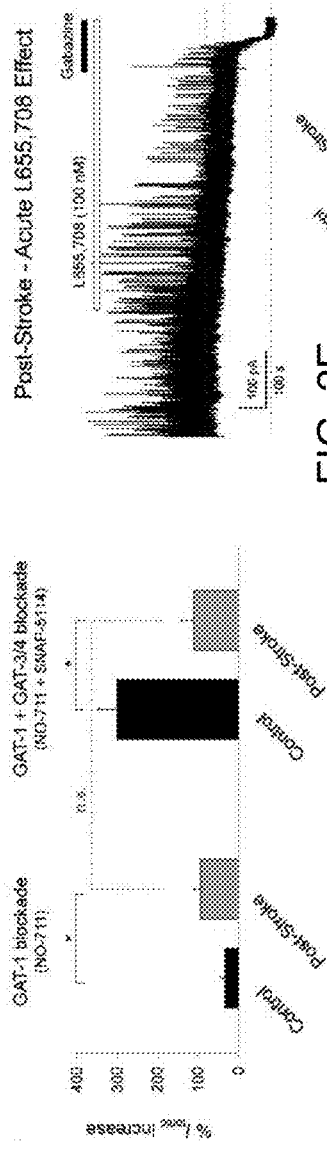
Figure 2E:
Figure 2F:

Tonic inhibition is effectively controlled by the degree of extracellular GABA uptake through neuronal and astrocytic GABA transporters (GATs) (Walker and Semyanov, '08). A GAT-1-selective antagonist, NO-711 (10 µM) had a significantly greater effect (% $I_{tonic}$ increase after GAT blockade) in post-stroke neurons (94.0±16.3%, n=10) than in controls (34.3±11.4%, n=6; $P<0.01$; FIG. 2A). Co-application of NO-711 and the GAT-3/4-selective antagonist SNAP-5114 (40 µM) produced a substantial increase in $I_{tonic}$ in controls (300.6±46.0%, n=4; FIG. 2A), revealing the synergistic actions of GATs in the cortex as previously proposed. In post-stroke neurons, co-application only produced an effect (110.7±32.0%, n=5) similar to GAT-1 blockade alone ($P<0.68$; FIG. 2A), indicating a dysfunction in GAT-3/4 after stroke. Sequential blockade of the two GATs confirmed the post-stroke impairment, as peri-infarct $I_{tonic}$ showed no further response to GAT-3/4 blockade after the initial GAT-1 block, in contrast to responses shown in controls (FIGS. 2 B, C). L655,708 (100 nM) reduced $I_{tonic}$ (FIG. 2 D). L655,708 significantly decreased post-stroke $I_{tonic}$, and notably reverted $I_{tonic}$ to near-control level (asterisk: $P<0.05$; n.s.: no significance) (FIG. 2F).

Figure 3:
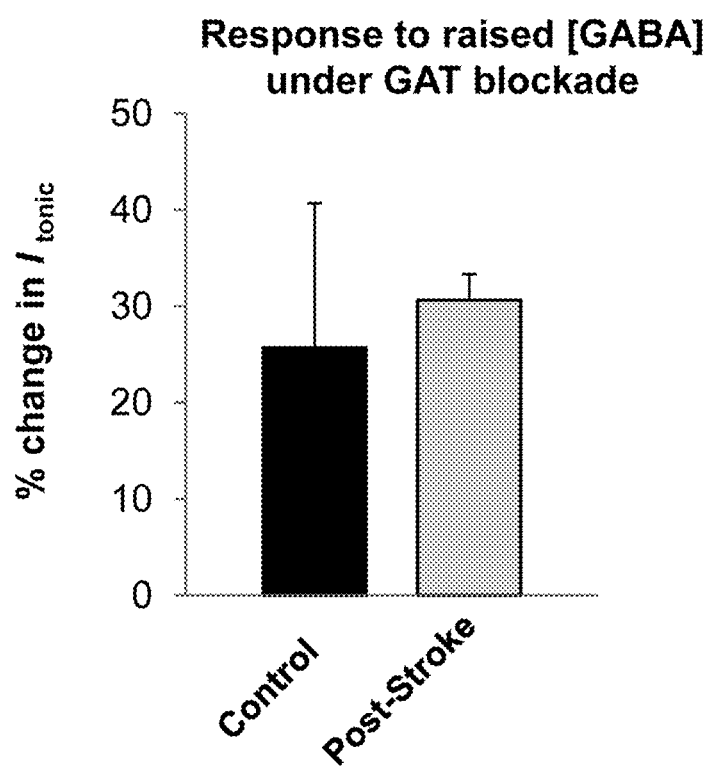
FIG. 3 shows additional analyses on the effects of GAT blockade and L655,708.

To demonstrate that $GABA_A Rs$ are not saturated after GAT blockade, GABA concentration in ACSF was raised (+10 µM) after blocking both GATs (by 10 µM NO-711+40 µM SNAP-5114). Graphs show the percent increase in $I_{tonic}$ (control: 25.7±15.0%, n=3; post-stroke: 30.6±2, 72%, n=3), indicating lack of receptor saturation in either control or post-stroke slices (FIG. 3).

Figure 4:
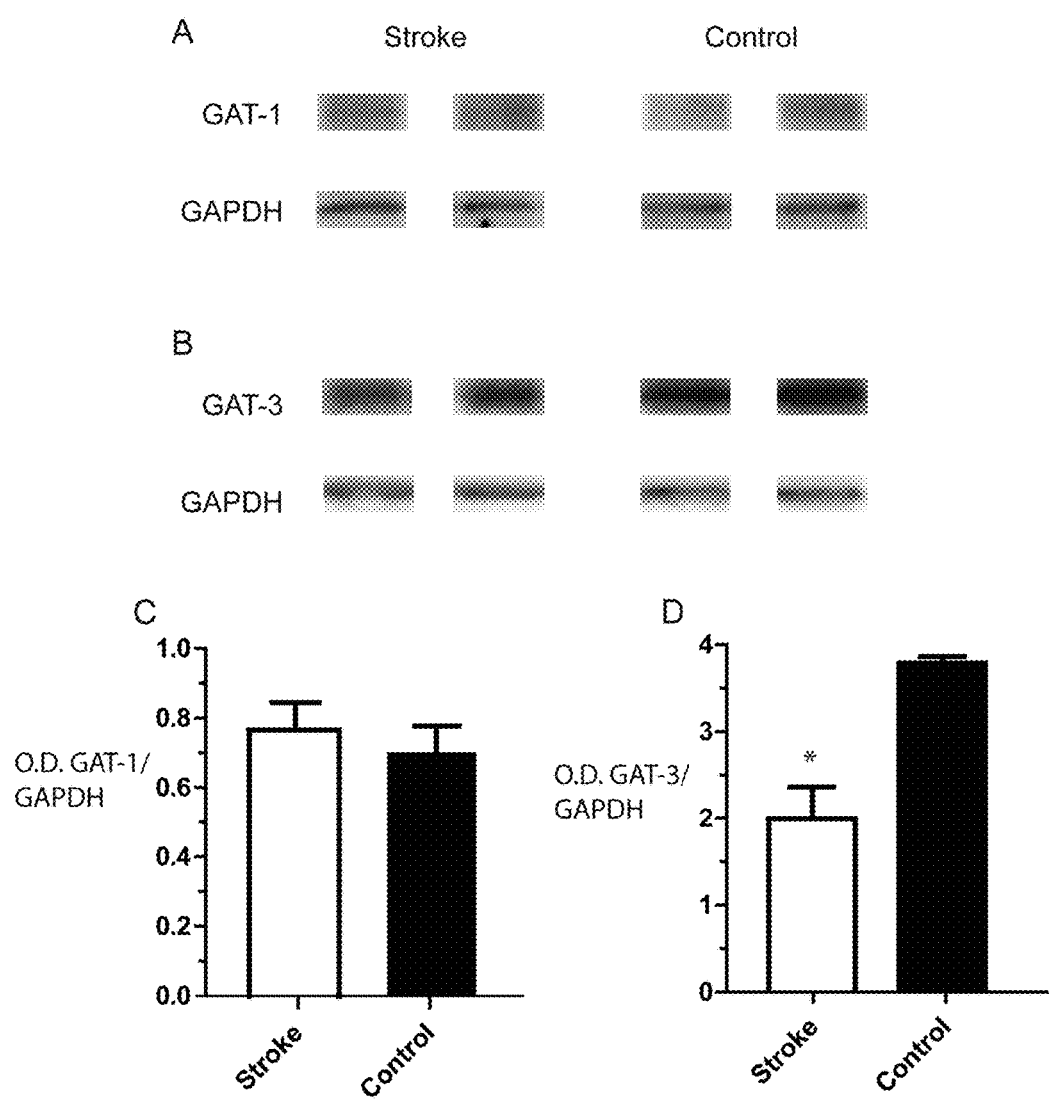
FIGS. 4A-4D depict GAT protein levels after stroke.

GAT-3/4 protein levels are reduced in peri-infarct motor cortex after stroke, whereas the GAT-1 levels are not changed (FIGS. 4A-4D). FIG. 4A shows a western blot of GAT-1 (top) and GAPDH (protein loading control, bottom). The blots are taken from two lanes from each condition. In all Western blot experiments for GAT-1 and GAT-3 (mouse GAT-4) samples were taken from five stroke animals and three controls. All Western blots were run in triplicate. FIG. 4B shows western blot of GAT-3/4 (top) and GAPDH (bottom). The lanes are in the same configuration as FIG. 4A. FIG. 4C shows quantification of GAT-1 protein level in a ratio to GAPDH in control and stroke. There is no significant difference between stroke and control for GAT-1 (p=0.45). FIG. 4D shows quantification of GAT-3/4 protein level in a ratio to GAPDH (1/GAPDH) in control and stroke. GAT-3/4 is significantly reduced in peri-infarct cortex (*=p=0.01). Each Western blot was run in triplicate.

Example 2

Stroke Model

Figure 5:
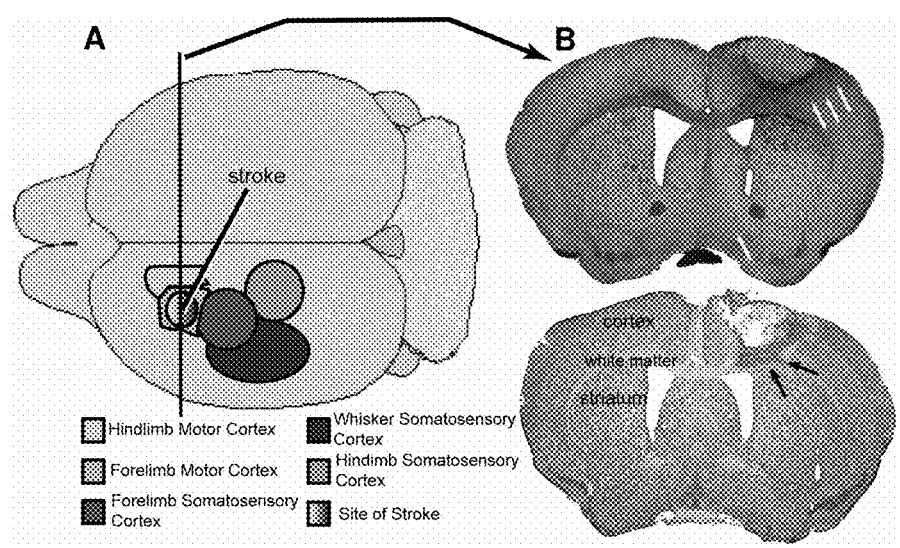
FIG. 5A is a schematic view of the motor control areas in the mouse cortex.
FIG. 5B provides two coronal sections through the frontal cortex.

Stroke completely destroys the tissue in at the center of the stroke (the core) and partially damages the tissue adjacent to the infarct (Katsman D, Spinelli K, Zhang J, and Carmichael S T (2003) Tissue microenvironments within functional cortical subdivisions adjacent to focal stroke. J Cereb Blood Flow Met 23:997-1009; Carmichael S T, Archibeque I, Luke L, Nolan T, Momiy J, Li S. (2005) Growth-Associated Gene Expression after Stroke: Evidence for a growth-promoting region in peri-infarct cortex. Expt Neurol. 193:291-311), i.e., the peri-infarct region. Studies indicate that this peri-infarct region is disabled through partial damage to neuronal circuits, as described above. To model this process experimentally, a stroke model was used that produces complete damage to a part of the brain that controls forelimb use in a mouse, the forelimb motor cortex (FIGS. 5A-5B). FIG. 5A shows a schematic view of the motor control areas in the mouse cortex. The stroke destroys part of the forelimb motor cortex. The vertical line indicates site of tissue sections in the middle panel. FIG. 5B shows two coronal sections through the frontal cortex, showing the stroke as seen in a stain for glial fibrillary acidic protein (GFAP, a marker of astrocytes) and cresyl violet (or a "Nissl" stain for cell bodies, bottom). The stroke damage is restricted to the cortex, with partial damage in adjacent white mater and surrounding motor areas. This damage is seen as increased staining for GFAP (reactive astrocytes, arrows) and increased cellularity in Nissl stains (arrows). This stroke knocks out part of the forelimb motor cortex and causes partial damage to the rest of forelimb cortex and to hindlimb motor cortex. This disables fore- and hindlimb control and produces weakness in using these limbs for walking and for exploratory forelimb behaviors, (such as using the forelimb when rearing onto objects, FIGS. 6A-6C). Measures of fore- and hindlimb behaviors in this model of stroke thus provide a readout of the function of partially damaged brain areas near the stroke core.

Example 3

Effect of GABAaRα5 Inverse Agonist

To test the role of tonically active GABA receptor signaling in stroke recovery, the GABAaRα5 inverse agonist (L655,708) was administered beginning three days after stroke. This time period was chosen because it is after the period of most cell death in this stroke model (Braun J S, Jander S, Schroeter M, Witte O W, Stoll G (1996) Spatiotemporal relationship of apoptotic cell death to lymphomonocytic infiltration in photochemically induced focal ischemia of the rat cerebral cortex. Acta Neuropathol. 92:255-63) and represents a high-value translational target for human stroke therapies. Treatments that must be administered very early in the clinical course of stroke, such as tPA, are difficult to deliver because most patients are not in the hospital and so rapid emergency response and laboratory screening systems must be developed. In contrast, drugs that are truly acting as a neural repair therapy may be delivered at later time points when most patients are in the hospital and are clinically stable.

The GABAaα5 inverse agonist L655,708 was administered through subcutaneously implanted osmotic minipumps. Mice were tested fore- and hindlimb function before, and then at one, two, four and six weeks after stroke.

Figure 6:
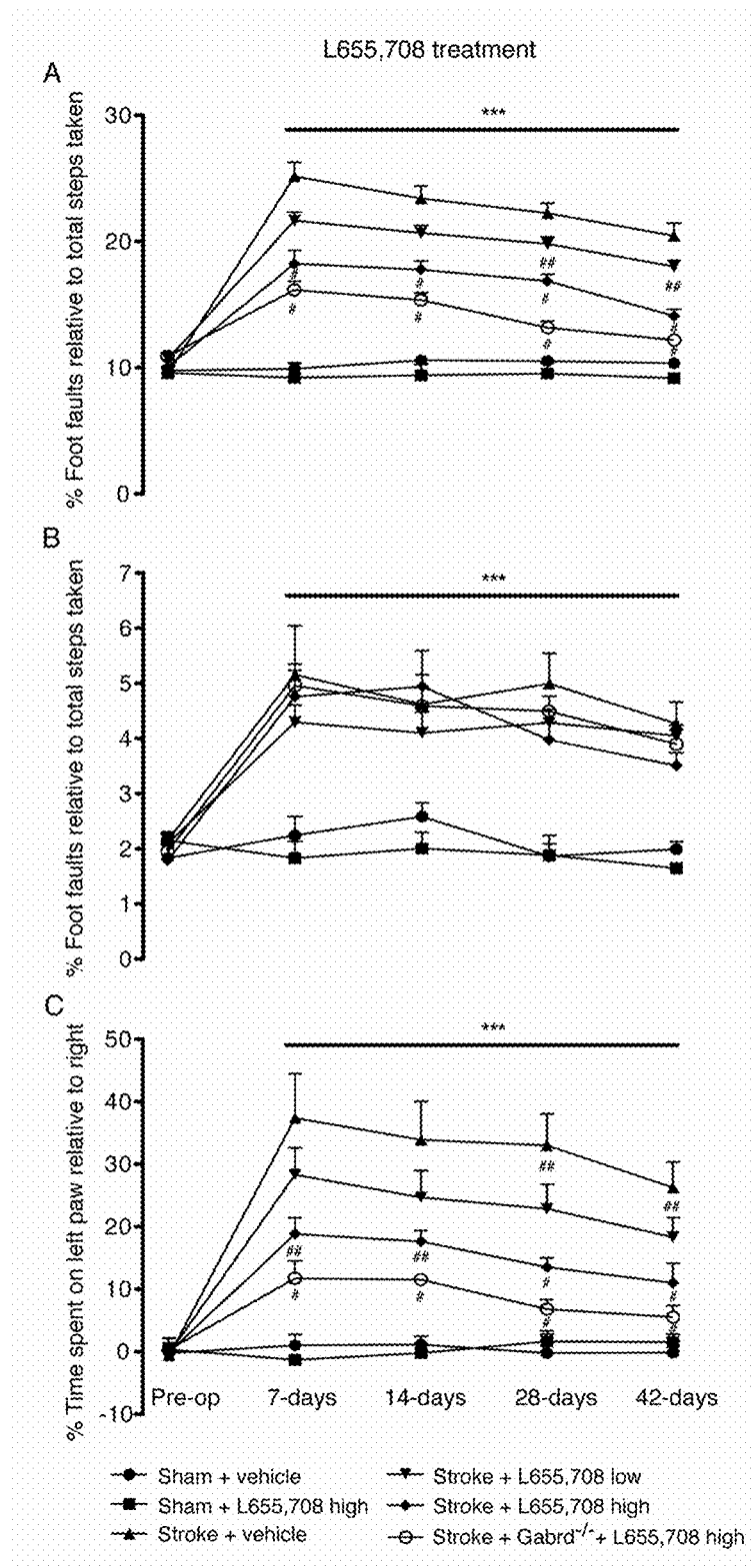
FIGS. 6A-6C illustrate behavioral recovery after stroke with L655,708.

FIGS. 6A to 6C illustrate behavioral recovery after stroke with L655,708. (Low dose L655,708=approximately 200 μg/kg/day per animal; high dose L655,708=approximately 400 μg/kg/day per animal. (For FIGS. 6A-6C and 8A-8C: Data are mean±s.e.m. n=8 per group for L655,708 and n=10 per group for GABAA receptor α5 subunit null mutant (Gabra5$^{-/-}$) and GABAA receptor δ subunit null mutant (Gabrd$^{-/-}$) animals, ***=P≤0.001 for stroke+vehicle vs Sham; +=P≤0.05, ##=P≤0.01, #=P≤0.001 vs stroke+vehicle). FIG. 6A shows forelimb function in the grid-walking task. After stroke, mice displayed significant foot faults on the grid. Treatment with L655,708 enhanced forelimb use, beginning on the first testing session. FIG. 6B shows that mice also displayed deficits in control of the hindlimb in this stroke model in the grid-walking task. Though the stroke is centered within the forelimb motor cortex, the hindlimb cortex was partially damaged. Mice showed significant footfaults with the hindlimb that do not statistically improve over time. Treatment with L655,708 resulted in statistically significant improvement by the 42 day testing period. FIG. 6C shows forelimb function in the "cylinder task" which measure spontaneous forelimb use when rearing. The Y axis shows symmetry of use of two forelimbs. Before stroke, mice used both forelimbs equally in rearing and exploring. After stroke, mice that received vehicle administration did not use the contralateral forelimb (right forelimb). This improved slightly over time. In contrast, mice that received L655,708 recovered right forelimb use very quickly, within several days of drug administration (at the 7 day post-stroke test period).

Figure 7:
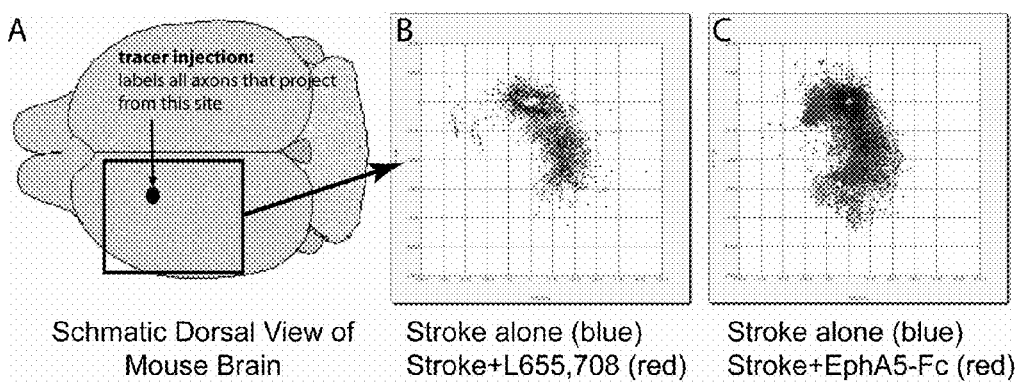
FIGS. 7A-7C illustrate patterns of cortical connections in control and in conditions of a basal/tonic GABA receptor inhibition.

FIGS. 7A-7C illustrate patterns of cortical connections in control and in conditions of a basal/tonic GABA receptor inhibition. In FIG. 7A, small injections of the neuroanatomical tracer BDA were placed into portion of the forelimb motor cortex that is adjacent to the stroke site 6 weeks after stroke. The location of all labeled cell bodies in the forelimb motor cortex, forelimb and hindlimb somatosensory cortex and facial (whisker) somatosensory cortex (highlight box) were digitally plotted. FIG. 7B. These plots convert the location of all the axonal connections of forelimb motor cortex into x/y plots, which were then grouped according to treatment condition and statistically compared among groups (Hotellings inverse T matrix). Plots show the location of labeled axons in groups of animals (n=5 for each condition). For L655,708 treated mice there is no difference in the pattern of axonal connections in peri-infarct cortex compared with stroke+vehicle. FIG. 7C. Plot of axonal connections in which an EphrinA5 antagonist was delivered into the brain after stroke. This approach enhances the formation of new patterns of local connections in peri-infarct cortex. Stroke+EphA5-Fc (Red) and Stroke+vehicle (blue).

Figure 9:
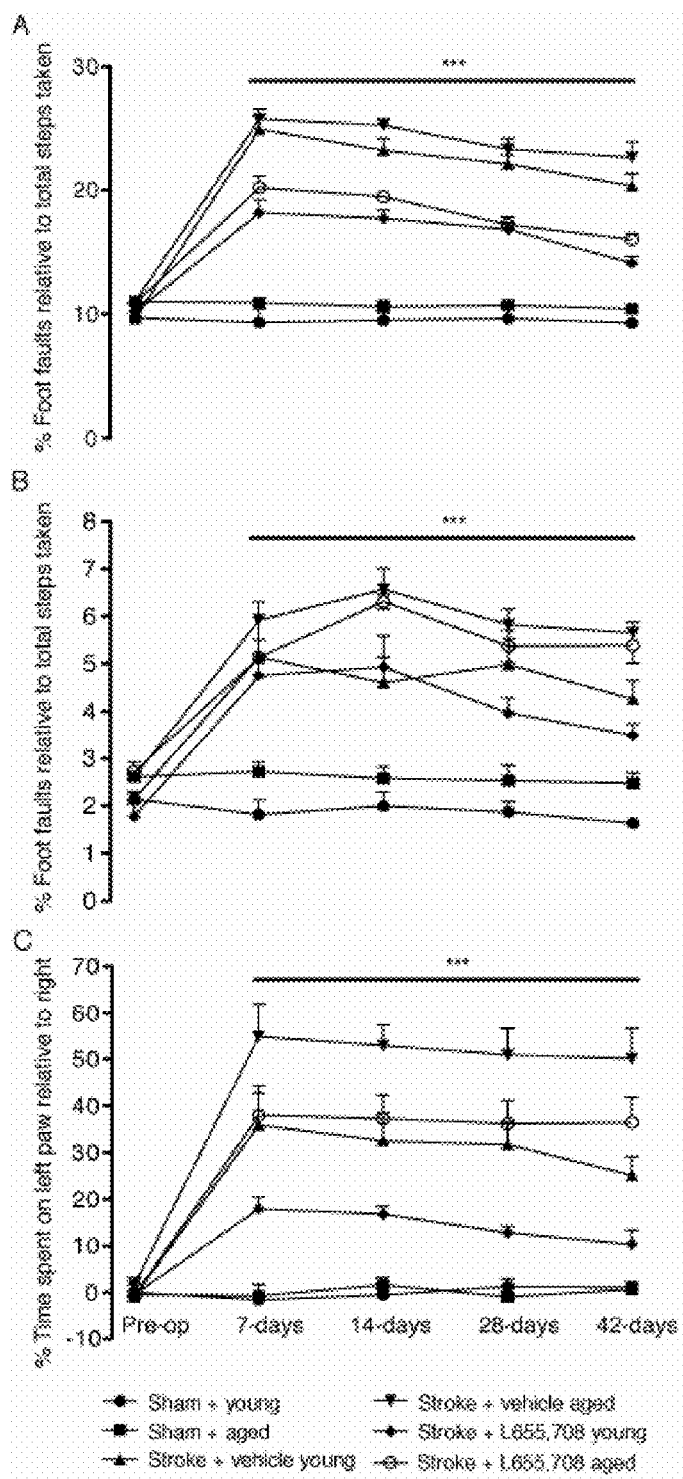
FIGS. 9A-9C illustrate behavioral recovery after stroke in young and aged animals with L655,708.

FIGS. 9A-9C illustrate behavioral recovery after stroke in young and aged animals with L655,708. L655,708 starting from 3-days after stroke resulted in an increase in functional recovery in both young and aged animals (FIGS. 9A-9C). Functional recovery was assessed behaviorally on both the gridwalking task for forelimb footfaults (FIG. 9A) and hindlimb footfaults (FIG. 9B), and on the cylinder task for forelimb asymmetry (FIG. 9C). The aged animals showed a greater impairment with increased numbers of hindlimb footfaults on the gridwalking task (FIG. 9B; P≤0.05) and in the inability to place the left-impaired forepaw onto the cylinder walk in the cylinder task (FIG. 9C; P≤0.01) for both vehicle a L655,708-treated groups. On average the normal gain of function in the aged stroke+vehicle treated animals is less than that of the young stroke+vehicle treated animals. In addition, the aged stroke+L655,708 animals show slightly less improvement compared to young stroke+L655,708 animals. For instance, on the cylinder task young stroke+L655,708 animals show a 15-18% gain of function post-stroke (7 to 42-days), compared with a 13-16% gain of function post-stroke in the aged. Data is shown as mean±s.e.m. for n=8 per group for L655,708 treatment for both young and aged animals, ***=P≤0.001 for stroke+vehicle vs Sham; +=P≤0.05, ++=P≤0.001 aged stroke+L655,708 vs aged stroke+vehicle, ##=P≤0.01, #=P≤0.001 young stroke+L655,708 vs young stroke+vehicle.

Figure 10:
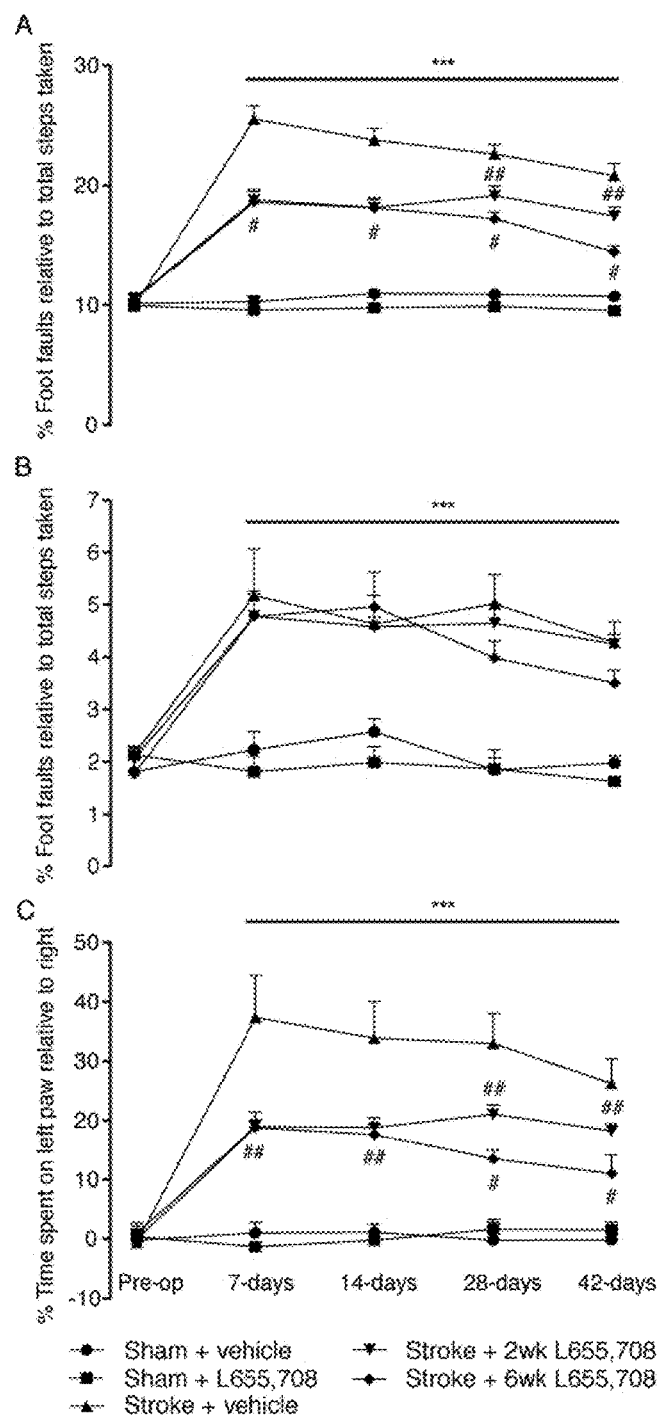
FIGS. 10A-10C depict the effect of two-week L655,708 treatment on functional recovery.

FIGS. 10A-10C depicts effect of two-week L655,708 treatment on functional recovery.

Functional recovery was assessed behaviorally on both the gridwalking task for forelimb footfaults (FIG. 10A), hindlimb footfaults (FIG. 10B), and on the cylinder task for forelimb asymmetry (FIG. 10C). Data are shown as mean±s.e.m. for n=8 per group, ***=P≤0.001 for stroke+vehicle vs. Sham; ##=P≤0.01, #=P≤0.001 vs. stroke+vehicle.

Two different durations of treatment were used (2 weeks and 6 weeks after stroke. Because stroke is a disease of aging, and the clinical target of stroke is most commonly aged patients, L655,708 was tested in aged animals after stroke. At the end of behavioral testing (6 weeks after stroke) mice received mapping of the pattern of cortical connections in the motor system in peri-infarct cortex (Overman J J, Kalaria S, Overman B, Willis D, Twiss J, Wanner I B, Li S, Carmichael S T (2008) Post-stroke blockade of ephrinA5 increases axonal sprouting in the mouse somatosensory cortex. Soc Neurosci. Abst.). Axonal sprouting in this peri-infarct cortex is closely associated with functional recovery in stroke (Carmichael, '06). Therapies directed toward neural repair after stroke promote the formation of new connections in peri-infarct cortex (Overman et al., '08). The mapping of cortical connections in the GABAaRα5 inverse agonist and Gabra5$^{-/-}$ and Gabrd$^{-/-}$ mice was used to demonstrate that these approaches also induce the formation of new connections in peri-infarct cortex.

The data demonstrate that a GABAaRα5 inverse agonist promotes behavioral recovery after stroke in a dose-dependent manner in both young adult (FIGS. 6A-6C) and aged mice (FIGS. 10A-10C). Further, by altering the dosing duration, it is seen that both 2-week and 6-week of blockade of GABAA receptor α5 after stroke produces behavioral recovery, with 6-week blockade producing the most significant recovery (FIGS. 10A-10C).

Example 4

Role of GABA$_A$ α5 and δ Receptors in Functional Recovery after Stroke

Figure 8:
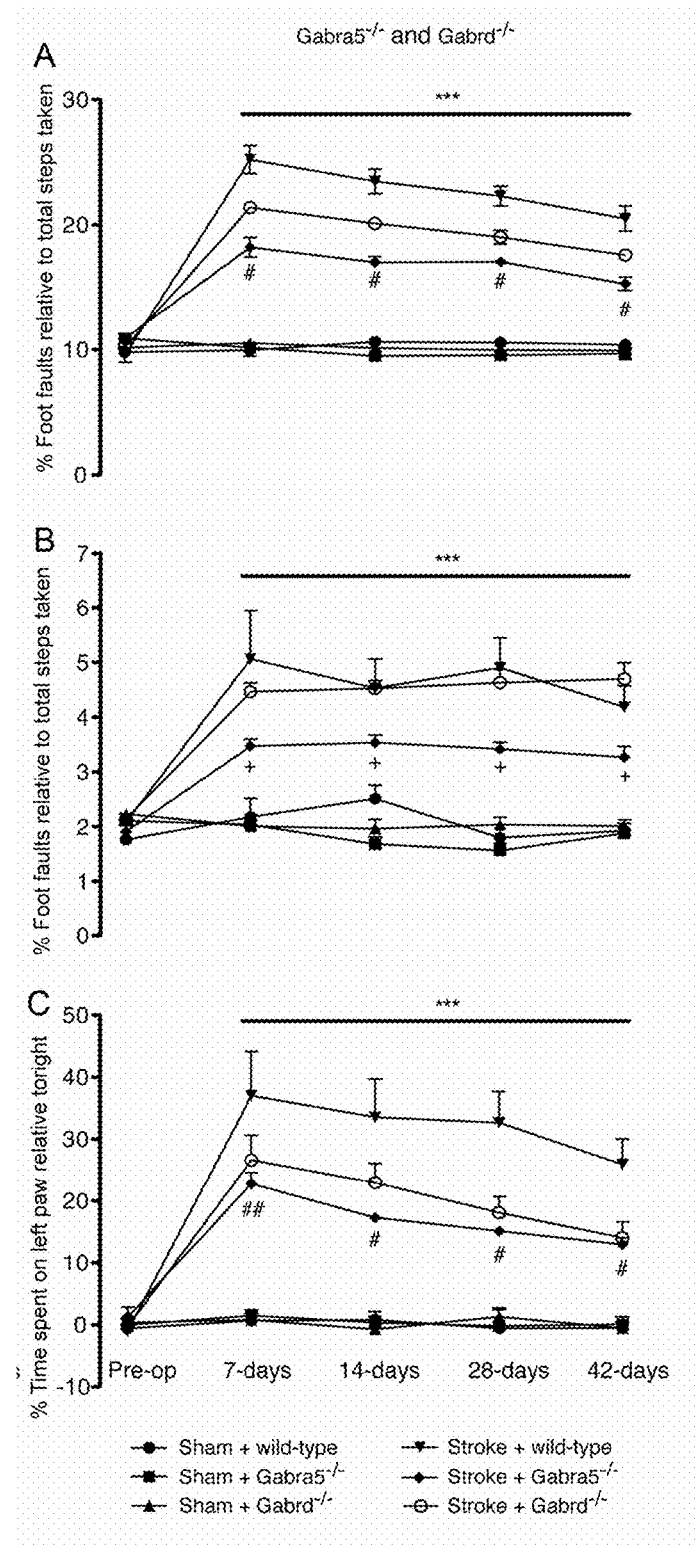
FIGS. 8A-8C illustrate that Gabra5$^{-/-}$ and Gabrd$^{-/-}$ mice have improved recovery of function after stroke.

To define the total role of GABA$_A$ α5 and δ receptors in functional recovery after stroke, behavioral testing was performed on Gabra5$^{-/-}$ and Gabrd$^{-/-}$ mice (FIGS. 8A-8C). For both α5 and δ knockouts, the same experimental approach was utilized. Mice were tested for e- and hindlimb function before stroke. One cohort was given a stroke in forelimb motor cortex, a second cohort served as control.

FIGS. 8A-8C illustrate that Gabra5$^{-/-}$ and Gabrd$^{-/-}$ mice have improved recovery of function after stroke. In both genetic knockout cases there is a statistically significant increase in both forelimb and hindlimb function after stroke compared to control stroke cohorts. (For FIGS. 6A-6C & 8A-8C: Data are mean±s.e.m. n=8 per group for L655,708 and n=10 per group for Gabra5-/- and Gabrd-/- animals, ***=P≤0.001 for stroke+vehicle vs Sham; +=0.05, ##=P≤0.01, #=P≤0.001 vs stroke+vehicle.). Also note that administering L655,708 to Gabard$^{-/-}$ mice has an additive effect on functional recovery, above that seen with GABAAR subtypes are playing a role in stroke recovery. FIGS. 8A and 8B. Grid-walking function for forelimb (FIG. 8A) and hindlimb (FIG. 8B) before and up to 6 weeks after stroke in GABAaRα5. FIG. 8C. Cylinder task function before and after stroke.

Administration of L655,708 to Gabrd$^{-/-}$ mice results in further functional recovery after stroke (FIGS. 6A to 6C) indicating that both blocking both α5 and δ GABAA receptors contribute to functional recovery and establishing both receptors as targets for stroke recovery.

After the completion of behavioral testing (6 weeks), mice received a microinjection of BDA into the forelimb motor cortex, and the position of labeled cell bodies was plotted into x/y coordinates and compared across groups. As with L655,708 there is no change in the pattern of axonal connections in peri-infarct cortex with either of these genetic manipulations after stroke.

The studies detailed above show that either pharmacological or genetic inhibition of tonic GABA receptor signaling improves behavioral recovery after stroke. The pattern of behavioral improvement occurs within days of starting the treatment. This very early effect on behavioral recovery is unique for neural repair treatment following a stroke. All other published studies of neural repair therapies, such as with erythropoietin, GM-CSF or stem/progenitor cell therapy, improve behavioral recovery gradually over time (Wang et al., '04, Stroke. 2004; 35: 1732; Shen L H, Li Y, Chen J, Cui Y, Zhang C, Kapke A, Lu M, Savant-Bhonsale S, Chopp. M (2007) One-year follow-up after bone marrow stromal cell treatment in middle-aged female rats with stroke. Stroke. 38:2150-6; Minnerup J, Heidrich J, Wellmann J, Rogalewski A, Schneider A, Schäbitz W R. Meta-analysis of the efficacy of granulocyte-colony stimulating factor in animal models of focal cerebral ischemia. Stroke. 39:1855-61). Tonically active GABAa receptor inhibition improves function not only for the region directly damaged in the stroke site, but also for hindlimb function, which derives from a part of motor cortex that is partially damaged and in peri-infarct cortex.

The treatment applications of the present invention may therefore be employed to treat partially damaged neuronal circuits in the peri-infarct cortex since the effect on behavioral recovery occurs early in stroke, involves peri-infarct areas and does not involve axonal sprouting. Further, the present invention may be extended to any type of inhibition approach (e.g., pharmacological or genetic) which alters basal or tonic GABA signaling to improve recovery after stroke or another CNS injury.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, That which is claimed is:

1. A method of treating one or more pathological injuries selected from the group consisting of a stroke and ischemic brain damage in a subject, the method consisting of:
administering to the subject an effective amount of a gamma aminobutyric acid (GABA) receptor signaling inhibitor that inhibits signaling from an α5 subunit containing GABA receptor or that inhibits signaling from a δ subunit containing GABA receptor, wherein the pathological injury is characterized by the presence of physically damaged or altered CNS tissue, wherein the administration does not begin until three days after the pathological injury occurs, and wherein the inhibitor is selected from the group consisting of:
6,6-Dimethyl-3-(2-hydroxyethyl)thio-1-(thiazol-2-yl)-6,7-dihydro-2-benzothiophen-4(5H)-one;

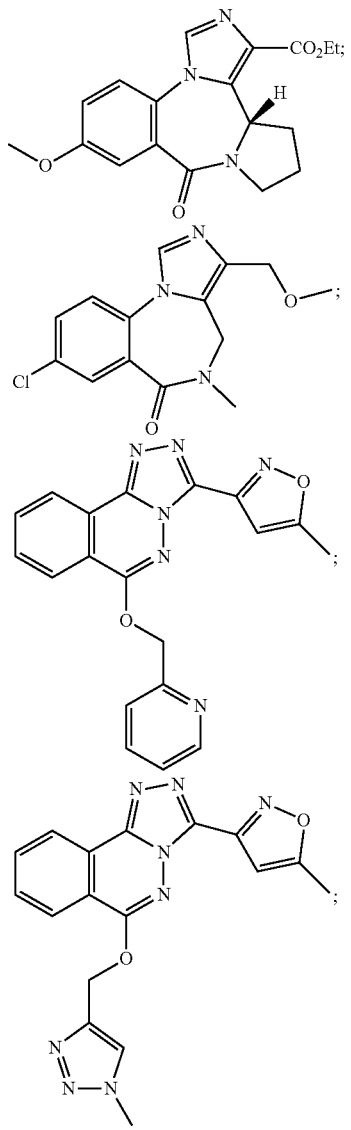

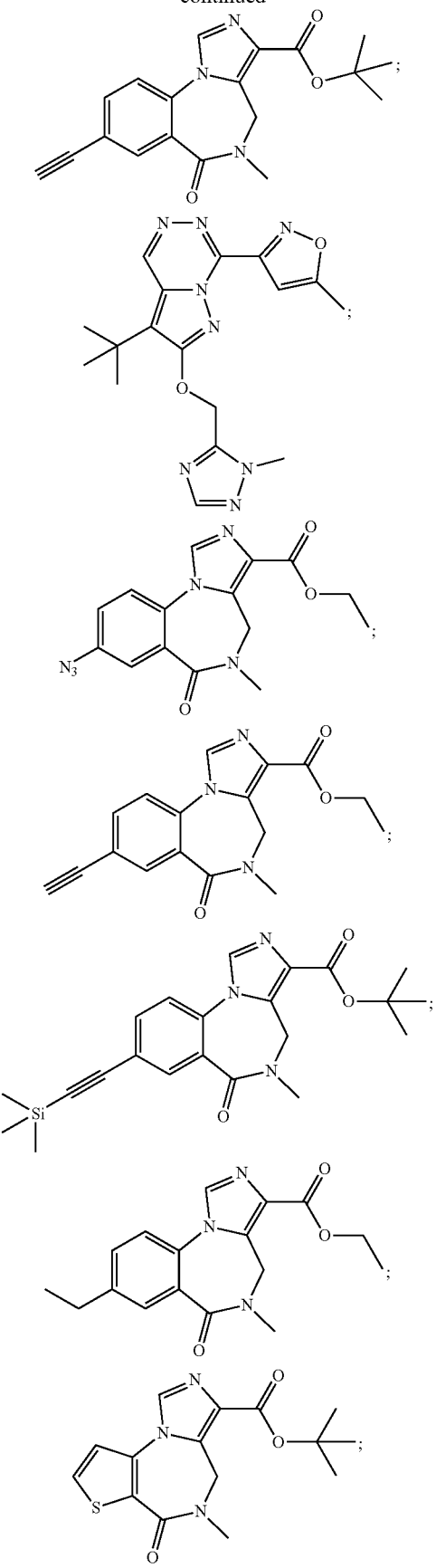

-continued

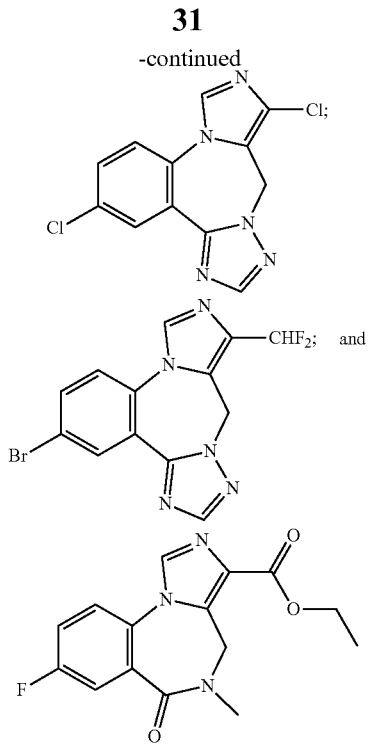

or a pharmaceutically acceptable salt thereof.

2. The method according to claim 1, wherein the GABA receptor signaling inhibitor is:

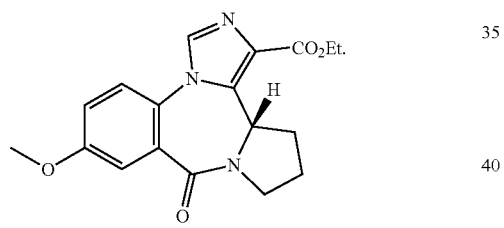

3. The method according to claim 1, wherein the subject is a human subject.

4. The method according to claim 1, wherein the stroke is ischemic stroke or hemorrhagic stroke.

5. The method according to claim 4, wherein the stroke is characterized by increased GABA receptor signaling in peri-infarct tissue.

6. A method of treating one or more pathological injuries selected from the group consisting of a stroke and ischemic brain damage in a human patient, the method consisting of:
diagnosing the patient as having the pathological injury and then administering to the patient having the injury an effective amount of a gamma aminobutyric acid (GABA) receptor signaling inhibitor that inhibits signaling from an α5 subunit containing GABA receptor or that inhibits signaling from a δ subunit containing GABA receptor, wherein the administration does not begin until three days after the pathological injury occurred, and wherein the inhibitor is selected from:

6,6-Dimethyl-3-(2-hydroxyethyl)thio-1-(thiazol-2-yl)-6,7-dihydro-2-benzothiophen-4(5H)-one;

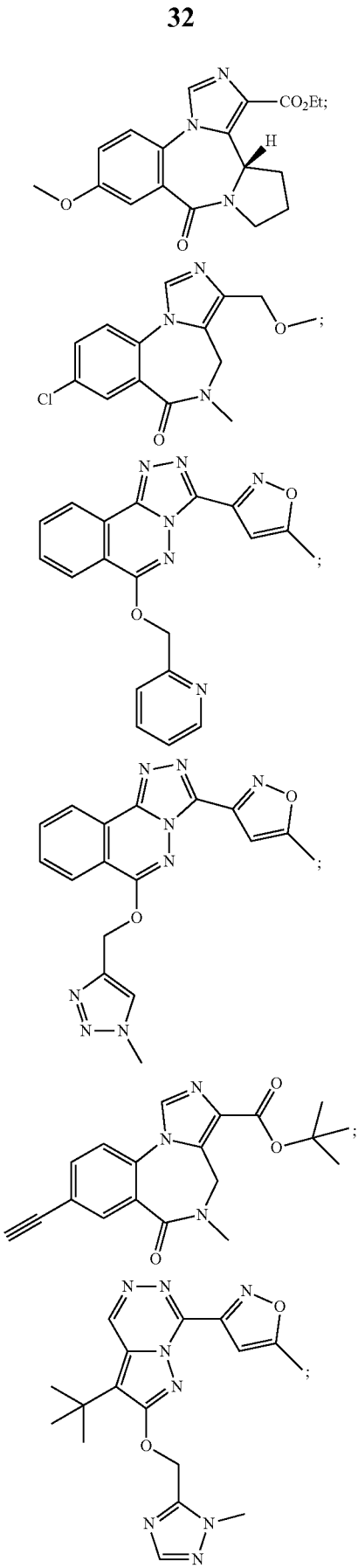

or a pharmaceutically acceptable salt thereof.

7. The method according to claim 6, wherein the GABA receptor signaling inhibitor is:

8. The method according to claim 6, wherein the subject is a human subject.

9. The method according to claim 6, wherein the stroke is ischemic stroke or hemorrhagic stroke.

10. The method according to claim 9, wherein the stroke is characterized by increased GABA receptor signaling in peri-infarct tissue.

11. A method of treating one or more pathological injuries selected from the group consisting of a, stroke and ischemic brain damage in a human patient, the method consisting of: assessing the subject for peri-infarct tissue repair and then administering to the patient an effective amount of a gamma aminobutyric acid (GABA) receptor signaling inhibitor that inhibits signaling from an a5subunit containing GABA receptor or that inhibits signaling from a d subunit containing GABA receptor, wherein the administration does not begin until three days after the pathological injury occurred, and wherein the inhibitor is selected from:

6,6-Dimethyl-3-(2-hydroxyethyl)thio-1-(thiazol-2-yl)-6,7-dihydro-2-benzothiophen-4(5H)-one;

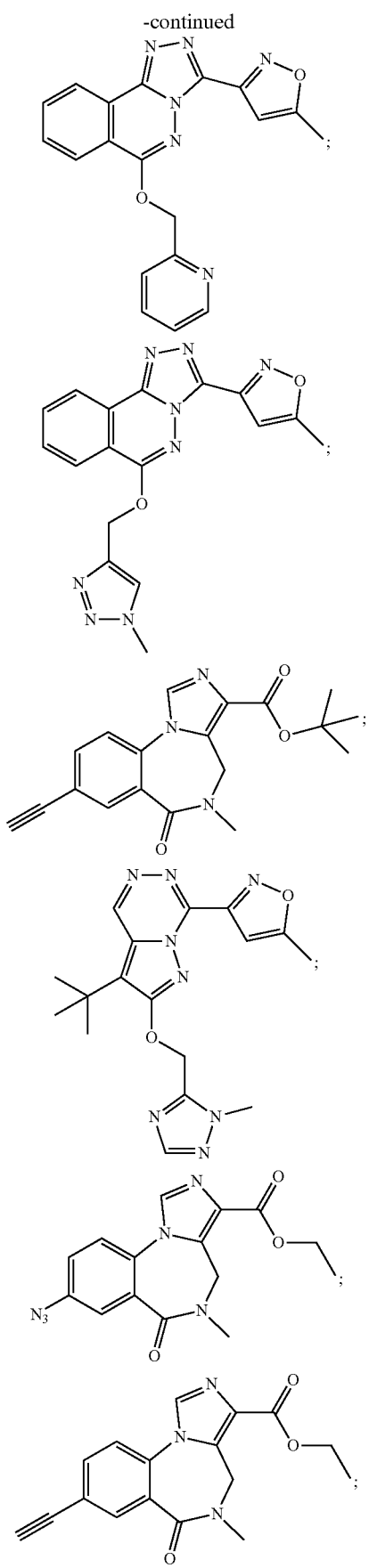
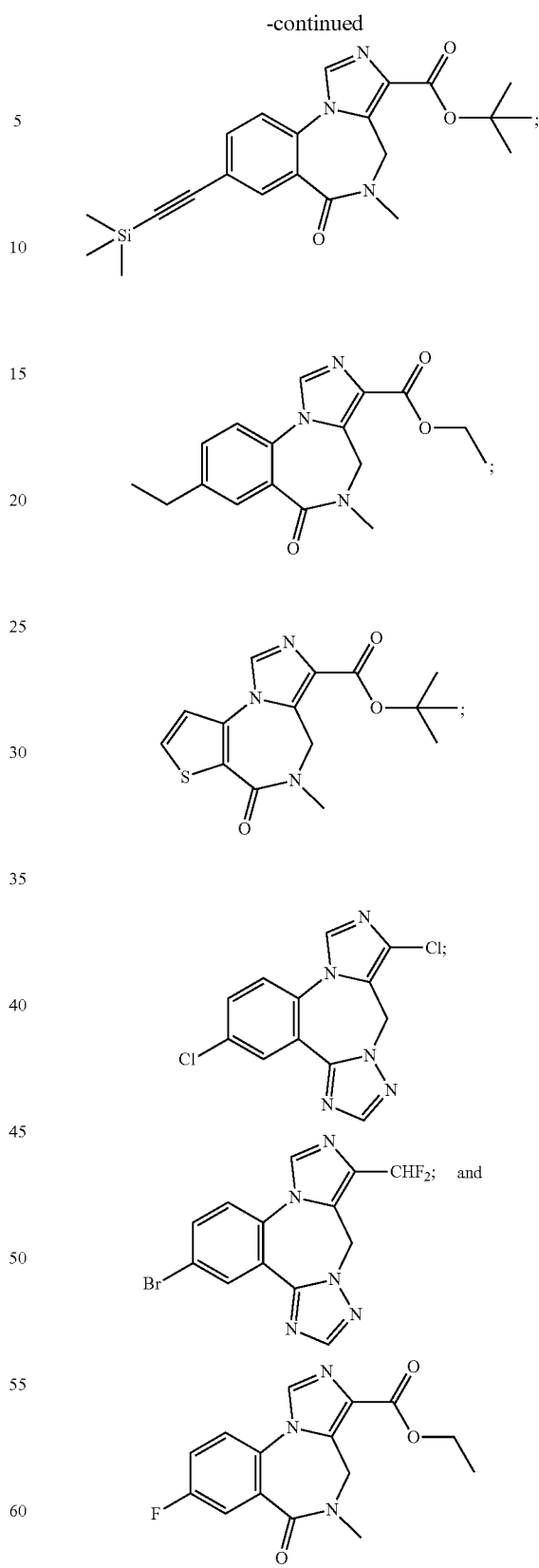
or a pharmaceutically acceptable salt thereof.
12. The method according to claim 11, wherein the GABA receptor signaling inhibitor is:

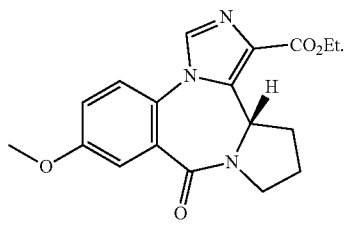 [SMILES: CCOC(=O)c1ncn2c1[C@@H]1CCCN1C(=O)c1cc(OC)ccc1-2]
13. The method according to claim 11, wherein the subject is a human subject.
14. The method according to claim 11, wherein the stroke is ischemic stroke or hemorrhagic stroke.
15. The method according to claim 14, wherein the stroke is characterized by increased GABA receptor signaling in peri-infarct tissue.
* * * * *